US 7,578,166 B2

(12) United States Patent
Ethridge et al.

(10) Patent No.: US 7,578,166 B2
(45) Date of Patent: Aug. 25, 2009

(54) ACOUSTIC TRANSDUCER CALIBRATION BLOCK AND METHOD

(75) Inventors: Roger E. Ethridge, Houston, TX (US); David A. Mandina, Belle Chassa, LA (US); Darko Kamenjasevic, Middelburg (NL); Christopher S. O'Neal, Metairie, LA (US)

(73) Assignee: Grant Prideco, L.P., Houston, TX (US)

( * ) Notice: Subject to any disclaimer, the term of this patent is extended or adjusted under 35 U.S.C. 154(b) by 9 days.

(21) Appl. No.: 12/013,583

(22) Filed: Jan. 14, 2008

(65) Prior Publication Data

US 2009/0178466 A1   Jul. 16, 2009

(51) Int. Cl.
*G01M 1/14* (2006.01)
(52) U.S. Cl. ........................................................ 73/1.82
(58) Field of Classification Search ........................ None
See application file for complete search history.

(56) References Cited

U.S. PATENT DOCUMENTS

| | | | |
|---|---|---|---|
| 4,470,307 A * | 9/1984 | Genter et al. | 73/634 |
| 4,576,034 A * | 3/1986 | Ferree et al. | 73/1.84 |
| 4,725,989 A | 2/1988 | Granz et al. | |
| 4,757,716 A | 7/1988 | Nottingham et al. | |
| 4,843,884 A * | 7/1989 | House et al. | 73/622 |
| 5,097,512 A * | 3/1992 | Batey | 381/58 |
| 5,665,893 A | 9/1997 | Smith | |
| 6,192,735 B1 | 2/2001 | Nagai | |
| 6,415,644 B1 | 7/2002 | Rockwood et al. | |
| 6,460,414 B1 | 10/2002 | Erickson et al. | |
| 6,938,457 B2 | 9/2005 | Johnson et al. | |
| 7,013,732 B2 | 3/2006 | McKeon | |
| 7,021,143 B2 | 4/2006 | Dasch | |
| 2005/0087581 A1 | 4/2005 | Otten et al. | |
| 2006/0191874 A1 | 8/2006 | Holdren | |
| 2006/0283250 A1 | 12/2006 | Fair et al. | |
| 2007/0044559 A1 * | 3/2007 | Andrews | 73/584 |

OTHER PUBLICATIONS

List of Phased Array Books by Olympus NDT, 2007.
TNT, The NDT Technician, Apr. 2003.
Special Phased Array Applications for Pipeline Girth Weld Inspections; Michael Moles and Simon Labbe, ECNDT 2006.
Ultrasonic Phased Array, Michael Moles, Olympus NDT, 2007.
Phased Array Instruments, Olympus NDT 2007.
Entering a New Phase in Weld Inspection, Michael Moles, The Fabricator, Oct. 3, 2006.

(Continued)

*Primary Examiner*—Robert R Raevis
(74) *Attorney, Agent, or Firm*—Williams, Morgan & Amerson, P.C.

(57) ABSTRACT

A calibration system is provided for calibrating acoustic transducers such as phased array acoustic transducers and time of flight acoustic transducers. In one embodiment, a calibration block is provided with predetermined calibration features defined therein. The calibration block may be provided with guide surfaces or engagement surfaces utilized to position the transducers accurately with respect to the calibration features so that the same acoustic scanning views are consistently produced. In one embodiment, the guide surfaces define a recessed region for acoustic couplant. The outputs can be combined to produce an image and compared to a known image to verify that the acoustic transducers are all oriented properly and calibrated for operation.

11 Claims, 7 Drawing Sheets

OTHER PUBLICATIONS

F and M Magazine, Aug. 24, 2007, Phased Array Ultrasonics, Used for the Right Application, Can Bring Significant Advantages to the Table, Michael Moles.

A Contribution to Repeatability of 1-D Linear Array Probes Used on Large Scale Inspection of Low-Pressure Turbine Components by Peter Ciorau, Sep. 2006.

Mechanised Ultrasonic Inspections of Pipeline Girth Welds, A Brief History, by E.A. Ginzel, NDT.net, Mar. 2000.

Automatic Ultrasonic Inspection of Pipeline Girth Welds with a Corrosive Resistant Alloy (CRA) Layer, by Van Der ENT, Findlay, Portzgen, Nupen, Endal and Forli, NDT, Nov. 2006.

* cited by examiner

ACOUSTIC TRANSDUCER CALIBRATION BLOCK AND METHOD

BACKGROUND OF THE INVENTION

1. Field of the Invention

The present invention relates generally to the field of acoustic scanning and, more specifically, to a calibration block system and method for calibration of acoustic transducers.

2. Description of the Background

Calibration blocks for calibrating acoustic transducers are well known. However, the inventors believe that prior art calibration blocks have many problems that result in difficult to solve calibration problems. These problems limit the potential effectiveness of acoustic, e.g., ultrasonic, transducers such as phased array acoustic transducers. The term "phased array" when used herein refers to phased array acoustic, e.g., ultrasonic, transducers.

In principle, phased array acoustic transducers should have important advantages over other non-destructive means to test welds. Phased array transducers may utilize multiple elements for quickly scanning material to be investigated from multiple angles. At least theoretically, phased array acoustic transducers should provide additional information as compared to other nondestructive means to test welds that should allow the user to obtain a much clearer picture of a feature such as a weld. An x-ray, for example, does not provide enough information to obtain a detailed 3-D picture of the internal features of the weld. Unfortunately, at least in the prior art, the accuracy and repeatability of phased array transducers is a significant problem. When attempts are made to utilize other types of transducer measurements in conjunction with phased array acoustic transducers, additional significant problems may arise.

Phased array acoustic transducers are highly sensitive to orientation. For instance, one or more of signal amplitude, signal velocity, and/or wedge delay information might be affected. Thus, the phased array output information is susceptible to significant variations with very slight changes in orientation. Ironically, the same sensitivity and amount of information, which is an advantage of phased array transducers, has also been a problematic disadvantage. Moreover, such systems tend to be very expensive, dedicated to a specific scanning purpose, and not readily adaptable to different scanning purposes. These problems and the high cost of such systems have limited their practical value for scanning welds.

In the prior art, when multiple phased array transducers are utilized, each transducer may be calibrated by orienting the transducer with respect to defects or features having a known geometry or structure. However, because the phased array transducers are so sensitive to their orientation, one or more of the orientations of the transducers may change as compared to that used during calibration. To attempt to determine which of multiple transducers is no longer calibrated correctly is difficult, time consuming, and ultimately may not be possible even after hours of work.

When attempting to combine outputs from different types of acoustic transducers, it has been difficult to match the readings. For instance, time of flight transducers may not be mounted in such a way that they are set to view the same features as a phased array transducer.

Good calibrations require the ability to repeat physical movement of the transducers with respect to known embedded features under conditions that do not change. Prior art calibrators and calibration techniques frequently introduce numerous variables into calibrations. These errors may include variations in the orientation of one or more of multiple phased array transducers, variations in acoustic couplant, variations in the encoder measurements, and other calibration variations, which ultimately result in an inconsistent testing of tubular welds.

When scanning large diameter tubulars, due to the time and cost of making welds, it is important that the means for verifying/certifying the weld is repeatable and accurate. Only in this way can welding techniques be developed that produce a consistently quality weld and reliable proof that the weld is acceptable for its intended purpose. Exemplary examples of large diameter welding machines, complex pipe/connector weld joints, methods of welding, and welding alignment devices are shown in US Publication No. 20060191874, to R. L. Holdren, entitled Pipe/Connector Weld Joint, And Methods Of Welding Same, and US Publication No. 20050087581, to Otten et al., entitled Welding Alignment Device, and Methods of Using Same, both publications assigned as is the present application, and both publications being hereby incorporated herein by reference for all purposes.

Consequently, there remains a long felt need for improved methods for calibration systems starting with an improved calibration block that provides more reliable and accurate acoustic transducer calibration. Those skilled in the art have long sought and will appreciate the present invention, which addresses these and other problems.

SUMMARY OF THE INVENTION

It is an objective of the present invention to provide an improved method and/or system for calibrating transducers.

Another potential objective of an embodiment of the invention may comprise an improved calibration block.

These and other objectives, features, and advantages of the present invention will become apparent from the drawings, the descriptions given herein, and the appended claims. However, it will be understood that above-listed and/or other objectives and/or advantages of the invention described herein are intended only as an aid in understanding aspects of the invention, are not intended to limit the claims to the invention in any way, and therefore do not form a comprehensive or restrictive list of objectives, and/or features, and/or advantages.

Accordingly, the present invention provides a calibration system for calibrating acoustic transducers. The invention may comprise a preferably metal block with one or more known defects or features embedded therein for calibrating the acoustic transducers when used to calibrate for non-invasively investigating metallic material. However, other materials may be used if desired.

In one embodiment, the invention may comprise one or more guide walls, such as engagement surfaces, positioned adjacent the known defects or features. The guide walls, such as engagement surfaces, may be provided at positions that place one or more acoustic transducers at a known position or positions or orientation relative to the known feature, defect, or defects. The guide wall or guide walls may be sufficient to position a transducer or simultaneously position multiple transducers at specific positions or along a predetermined path relative to the known features or defects to be acoustically scanned.

The calibration system may further comprise two or more guide walls. In another embodiment, the calibration system may further comprise a support secured to one or more acoustic transducers to thereby position the transducer or multiple transducers at one or more known positions, or at desired positions along a known calibration path relative to the one or more known features embedded within the calibration block.

In another embodiment, the guide wall(s) or engagement surfaces may define a portion of a watertight trap for acoustic couplant. In another embodiment, the known feature or features to be acoustically scanned for calibration purposes may be positioned within or beneath one or more watertight recessed regions formed within the calibration block. To align the acoustic transducers for repeatable, reliable calibrations, a support or support frame for acoustic transducers may be inserted into a mating receptacle formed by or within the watertight recessed region or regions.

In one embodiment, the metal block may define an intermediate portion between watertight recessed regions. This intermediate portion may be used by position sensors, such as a wheel or other position sensor, to provide position information with the output of the acoustic transducers. The calibration block may include features utilized to synchronize the position sensor, or to verify the location of the position sensor at a particular points, or the like. The position sensor may be of different types and comprise components such as one or more wheels, balls, and/or noncontact position sensors such as lasers, or the like.

In another embodiment, the present invention may comprise elements such as, for example, a metal block defining a plurality of known features embedded therein and/or a support frame for a plurality of acoustic transducers and/or a wheel pivotally connected to the support frame to engage the metal block and operable for movement in a first direction with respect to the support frame. If utilized, the pivotal wheel may be operable to pivot in another direction relative to the support frame for scanning a material to be investigated such as a weld.

In another embodiment, the metal calibration block may define one or more elongate slots. Corresponding elongate metal inserts may be mounted or secured within the one or more elongate slots. The known features or errors used for calibration may be embedded in the elongate metal inserts rather than or in addition to being embedded within the metal calibration block. In this way, the features used for calibration may be changed out, or the inserts may be replaced due to wear, or the like.

In another embodiment, a metal block may define at least one recessed region in which a plurality of the known features or "defects" is embedded for use in calibrating the acoustic transducers. The recessed region may be sized for receiving the acoustic transducers.

In another embodiment, the present invention may comprise a method for calibrating a plurality of acoustic transducers simultaneously. Steps might comprise mounting the plurality of acoustic transducers to a support frame and/or defining a plurality of known features within a metal block and/or positioning the support frame and the plurality of acoustic transducers against the metal block and/or recording respective outputs of the plurality of acoustic transducers in response to the plurality of known features and/or comparing the outputs to expected outputs in response to the known features. The method may or may not comprise moving the support frame with respect to the metal block, and/or recording respective outputs of the plurality of acoustic transducers with respect to a physical position of the plurality of acoustic transducers on the metal block.

In another embodiment, the method may comprise mounting the plurality of acoustic transducers to a support frame and/or defining a plurality of known features within a metal block and/or positioning the support frame and the plurality of acoustic transducers against the metal block and/or moving the support frame and the plurality of acoustic transducers with respect to the metal block to produce calibration signals from the plurality of acoustic transducers.

Other steps of an embodiment of the invention might comprise defining a recess within the metal block, and moving the support frame within the recess and/or moving the support frame relative to the metal block while the respective engagement surfaces are engaged to move the support frame along a predetermined path relative to the plurality of known features.

In yet another embodiment of the invention, a support frame may be provided that may support at least two acoustic transducers and may comprise at least two forks. Each fork may comprise two prongs, and a pivotal connection on each prong for connection with the acoustic transducers. A fork interconnection shaft may be utilized for connection with the two forks.

The two forks may be connected to the fork interconnection shaft at different distances with respect to each other to provide that a distance between the at least two forks is adjustable. In one embodiment, the support frame may further comprise a clamp housing integral with each of the at least two forks, the clamp housing being releasably securable to the fork interconnection shaft.

The acoustic transducers mounted to the support frame may comprise phased array acoustic transducers and/or time of flight acoustic transducers. The support frame may further comprise one or more additional fork interconnection shafts, which may be interconnected by one or more interconnection members to increase or decrease the number of transducers supported by the support frame.

In one embodiment, the support frame may comprise a clamp housing integral with each of the forks. As well, the shaft interconnection member may comprise at least two clamp housings for interconnection with at least two forks interconnection shafts.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged with certain features emphasized to facilitate an understanding of the invention. The drawings are not intended to limit the claims to the invention in any way but instead show particular embodiments that are believed to be useful to those of skill in the art to illustrate underlying concepts of the invention.

While the present invention will be described in connection with presently preferred embodiments, it will be understood that it is not intended to limit the invention to those embodiments. On the contrary, it is intended to cover all alternatives, modifications, and equivalents included within the spirit of the invention.

DESCRIPTION OF THE PREFERRED EMBODIMENTS

While descriptions of one or more embodiments are provided herein to illustrate concepts of the invention, it is to be understood that the present invention may be embodied in various forms. Therefore, specific details disclosed herein are not to be interpreted in a manner that limits the claims of the invention.

The present invention may provide a modular transducer support and/or a modular calibration block that may be utilized for accurately calibrating any number of acoustic transducers (signal sources) simultaneously. For instance, multiple transducers (signal sources) may be moved past or stationed at one or more embedded calibration features, the transducer outputs recorded with respect to position, whereupon that transducer's outputs may be combined or superimposed and compared to the expected results to verify the transducers (signal sources) are calibrated.

As used herein, transducers may comprise signal sources in various configurations. For example, in one possible embodiment a transducer may comprise a housing with one or more signal sources, e.g. five different data channels. Transducers may vary in construction with respect to various features which might, for example, comprise placement of pulse transmitter(s) and receiver(s) for a returned signal. As another example, each of separate housings of transducers 12 and 14 may or may not comprise multiple signal sources. In another embodiment, each of two transducers may each comprise three different signal sources. In one calibration method of an example of two transducers each having three signal sources, the six different signal sources may then be aligned based on position information and then merged to produce a picture of known features whereby the merged picture is then compared with expected results for the picture to verify that all six data sources are calibrated so as to cooperate with each other.

Calibrations may comprise calibrating various signal sources that may be recorded. Calibrations may comprise use of a calibration block to confirm previously made calibrations, e.g., at the beginning of a production shift, or may comprise use of a calibration block to provide a more in depth calibration and/or an initial calibration.

As one possible example for calibrating a plurality of phased array transducers, a calibration may comprise calibrating an encoder or physical position indicator. A delay of an acoustic signal, which may sometimes be referred to as a wedge delay, is calibrated. A velocity of an acoustic signal which may vary due to the speed of sound in the material(s) e.g., couplant, material boundaries, and the like, is calibrated. An amplitude of a received signal in response to a pulse from one or more directions to a particular shape/depth/relative angle of a calibration feature is calibrated.

As discussed hereinbefore, phased array transducers (signal sources) are extremely sensitive to any variation, which cause one or more of the above-described or other calibrations to be in error. In one possible embodiment, position information from a position sensor may be used to align signals from the plurality of transducers (signal sources) with respect to position, and then merge the position corrected respective outputs of the acoustic transducers to produce a merged output that can be compared with previous merged outputs. The merged output will only appear as it should if all transducers (signal sources) are properly aligned and cooperating together.

The modular transducer support structure may be adaptable to any number of phased array transducers, time of flight transducers, other types of transducers, and one or more position sensors. A transducer support structure may comprise modules of mounted transducers (signal sources) that may be connected or removed from other modules.

The modular support structure of one embodiment of the present invention may be adaptable to a desired number of different types of transducers (signal sources), and for scanning different types of structures and/or materials to be investigated. In another embodiment, a calibration block may be provided that may be utilized for simultaneously calibrating or simultaneously collecting information from various types and numbers of acoustic transducers.

Figure 1:
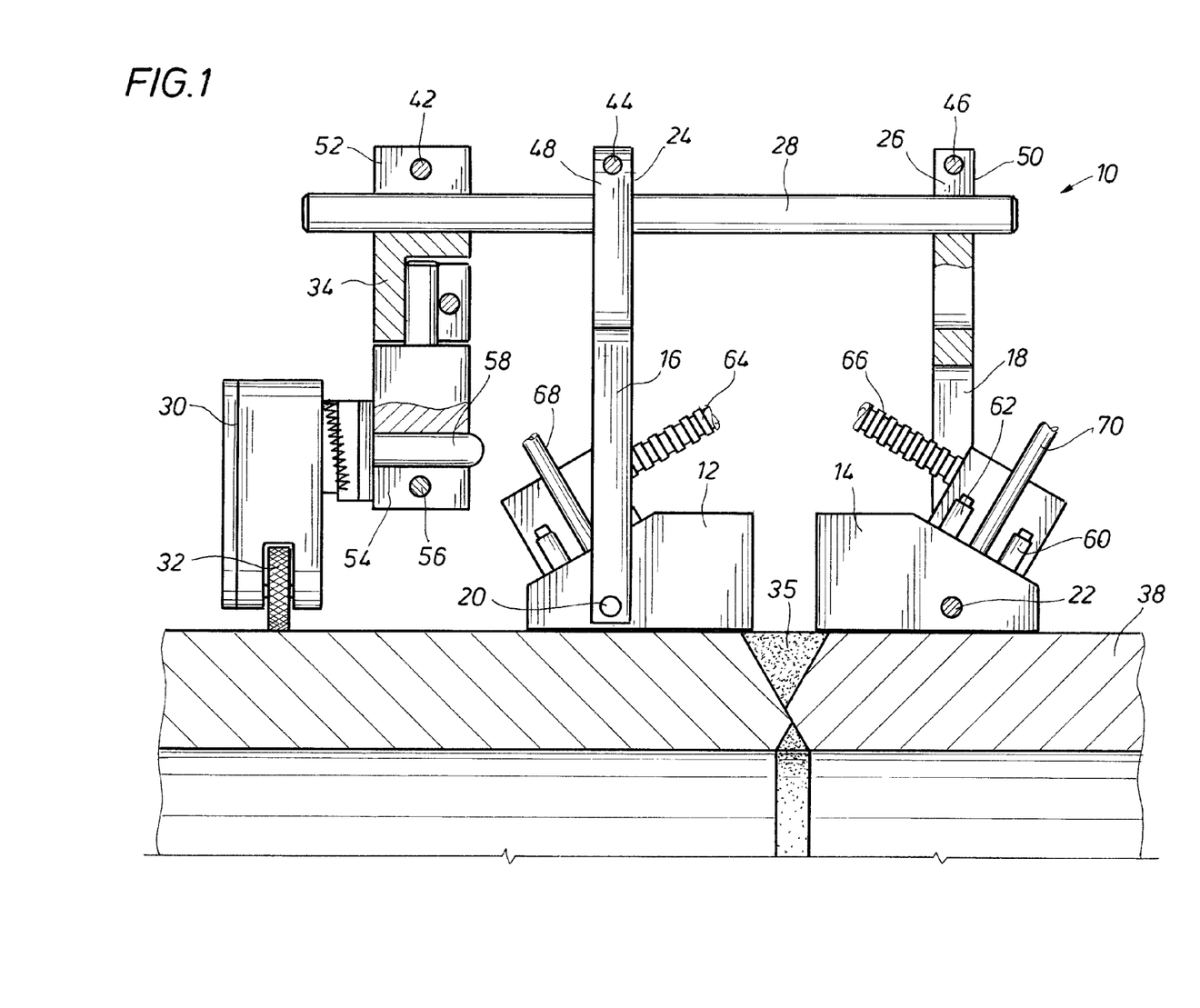
FIG. 1 is an elevational view, partially in section, illustrating an acoustic scanner frame for use in scanning a weld in accord with one possible embodiment of the invention.

Turning now to the drawings and more particularly to FIG. 1, there is shown one possible embodiment of support frame 10 that may be modified to support any number of transducers. The transducers (signal sources) mounted to support frame 10 may be of different types. For instance, support frame 10 may support phased array acoustic transducers, time of flight acoustic transducers, position sensors, encoders and other instrumentation, and/or other types of transducers. Support frame 10 preferably comprises metal interconnecting components but may utilize other materials such as plastics or the like.

In this particular nonlimiting embodiment, support frame 10 supports phased array acoustic transducers (signal sources) 12 and 14, although as noted above, other types of acoustic transducers and other types of transducers might also be supported by support frame 10. For example, only, the phased array transducers 12 and 14 may comprise thirty-two elements, and may scan over a range from 45 to 70 degrees. However, it will be appreciated by those of skill in the art that the invention may be utilized with other types of phased array transducers (signal sources) comprising a different number of elements in scanning over a different range.

Transducers (signal sources) 12 and 14 may be supported by respective forks 16 and 18 preferably utilizing pivotal connections, such as pivots 20 and 22. As used herein, a fork may be a bifurcated member divided into or made up of two extending legs or parts, or might comprise a support member with more than two legs, parts, arms, members, extensions, or the like, to support the transducers. Therefore, the term "fork" is not used in a limiting manner. In one embodiment, forks 16 and 18 may be generally or substantially u-shaped, as shown in the perspective view of the transducers (signal sources) and forks of support frame 10 of FIG. 3.

In one embodiment, pivots 20 and 22 may be positioned at or near the ends of the respective legs, parts, on arms, members, extensions, and the like, for connections with a lower portion of the respective phased array acoustic transducers (signal sources) 12 and 14. Pivots 20 and 22 permit phased array acoustic transducers (signal sources) 12 and 14 to move pivotally to conform to the surface of the material to be acoustically scanned.

The upper portion of forks 16 and 18, which may be referred to herein as fork ends 24 and 26, respectively, are shown in this example as being distal to phased array transducers (signal sources) 12 and 14. In this example, fork ends 24 and 26 are selectively interconnected together using a mechanical linkage, such as module shaft 28. Module shaft 28 may also interconnect encoder 30 with transducers (signal sources) 12 and 14. Shaft 28 may be any suitable structure, member, rod, or the like, to perform this function. Therefore, the term "shaft" is not limited to a particular construction. Module shaft 28 may be of different lengths, and may interconnect additional transducers.

In this example, nuts 42, 44, and 46 may be rotated to secure and/or release module shaft 28 from forks 16 and 18 and/or from encoder mechanism 30. In this embodiment, clamps 48 and 50 are integral with or built into fork ends 24 and 26, respectively. Clamp 52 may be integral with or built into encoder mechanism 30. Thus, clamps 48 and 50 may be viewed as comprising housings or clamp housings built into the fork ends. Other types of clamps, internal clamp housings, external clamp housings, and the like, might also be utilized for securing transducer support frame components together. However, the integral clamp construction shown here eliminates the need for additional clamp components and reduces the overall number of parts required for constructing support frame 10. This type of construction also provides a sturdy and convenient clamp for use in holding the various components of support frame 10 together.

Nuts 44 and 46, or other types of fasteners, may be utilized to tighten or loosen clamps 48 and 50. Nut 42 tightens or loosens encoder clamp 52. If desired, other types of fasteners, clamps, or the like, may be utilized for interconnecting module shaft 28 and/or other components of support frame 10.

Encoder mechanism 30 may be utilized as part of a position sensor. A position sensor may be provided so that transducer outputs (signal sources) may be recorded with respect to a position and/or with respect to multiple positions and/or with respect to position in a continuous movement. In this example, motion of encoder wheel 32 produces a digital position signal whereby the outputs of phased array transducers (signal sources) 12 and 14 may be recorded with respect to their physical position along weld 35. Encoder 30 produces position information along a single linear path. Other types of position sensors may be utilized including balls, lasers sensors, and the like, then provide position information over a surface, or in different linear directions, or the like. Means may be provided, such as position sensor marks and/or guide members, such as exactly positioned features, surfaces, clamps, stops, rails, walls, and/or the like, and may be built into a calibration block and/or provided by labels or the like, for determining a starting/measuring position and/or orientation, and/or for verifying various checkpoint positions, with respect to known calibration features.

Figure 3:
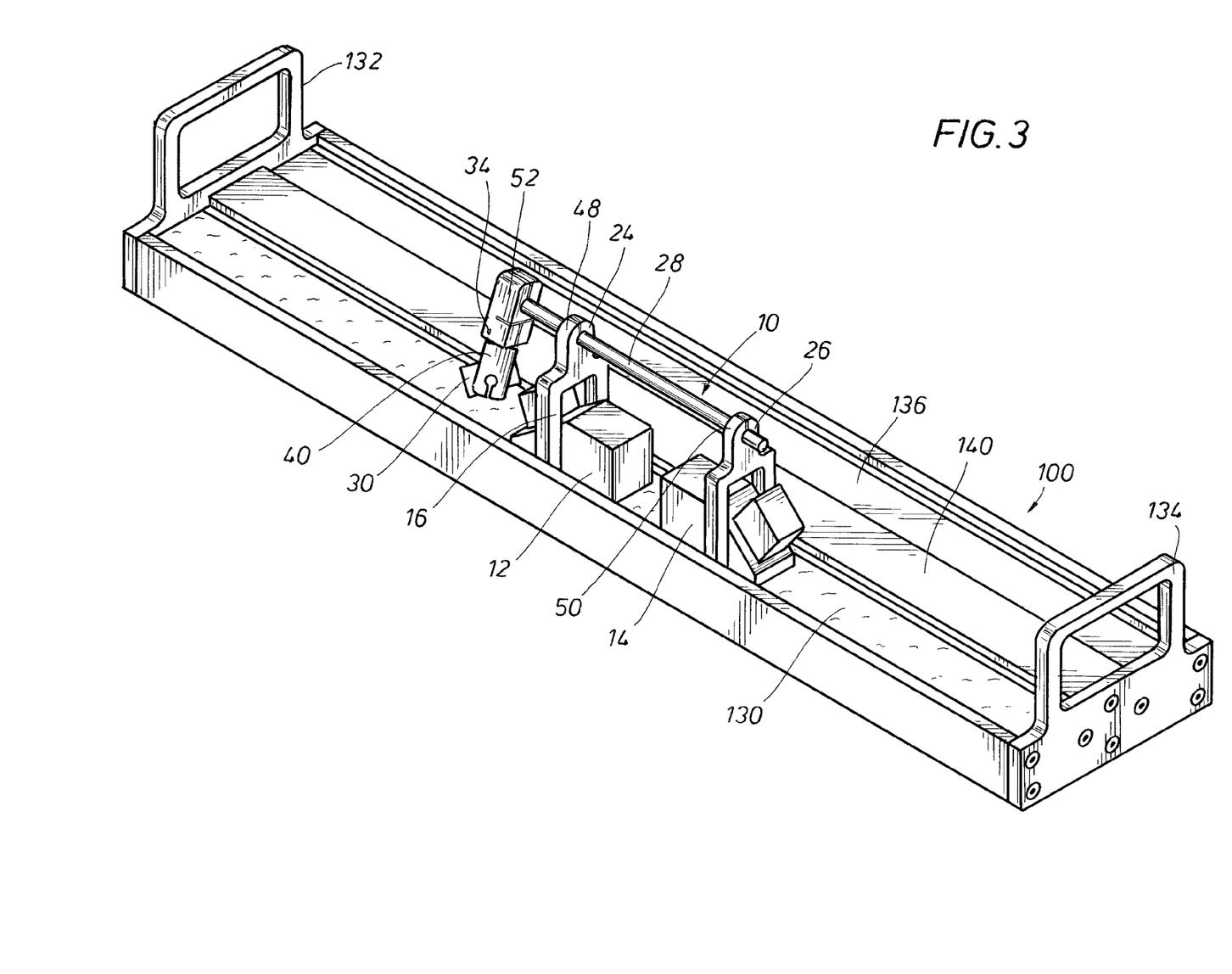
FIG. 3 is a perspective view of an acoustic scanner frame for use with a calibration block embodiment that may be utilized for calibrating multiple acoustic sensors of various types in accord with one possible embodiment of the invention.

In the embodiment of the position sensor shown in FIG. 1, if weld 35 extends into and out of FIG. 1, then wheel 32 may be oriented as shown to follow along weld 35 to measure the physical position at which the signals produced by transducers (signal sources) 12 and 14 are recorded. While an unwelded area is shown between radially inner and outer portions of weld 35, it will be understood that weld 35 extends through that area as well. It will be noted that in FIG. 1, the direction of wheel 32 is transverse to, and generally perpendicular to, the orientation of module shaft 28. Wheel 32 may be oriented at a right angle to that shown in FIG. 1, whereby the physical position is recorded when transducers (signal sources) 12 and 14 are moved in a direction parallel to module shaft 28, as indicated in FIG. 3. Accordingly, in this embodiment, wheel 32 is preferably pivotally connected for rotation in at least one axis, such as with wheel pivot connection 34. However, in other embodiments wheel 32 is pivotal in multiple different axis of rotation. In one embodiment, multiple pivotal connectors may be utilized for this purpose.

Figure 2:
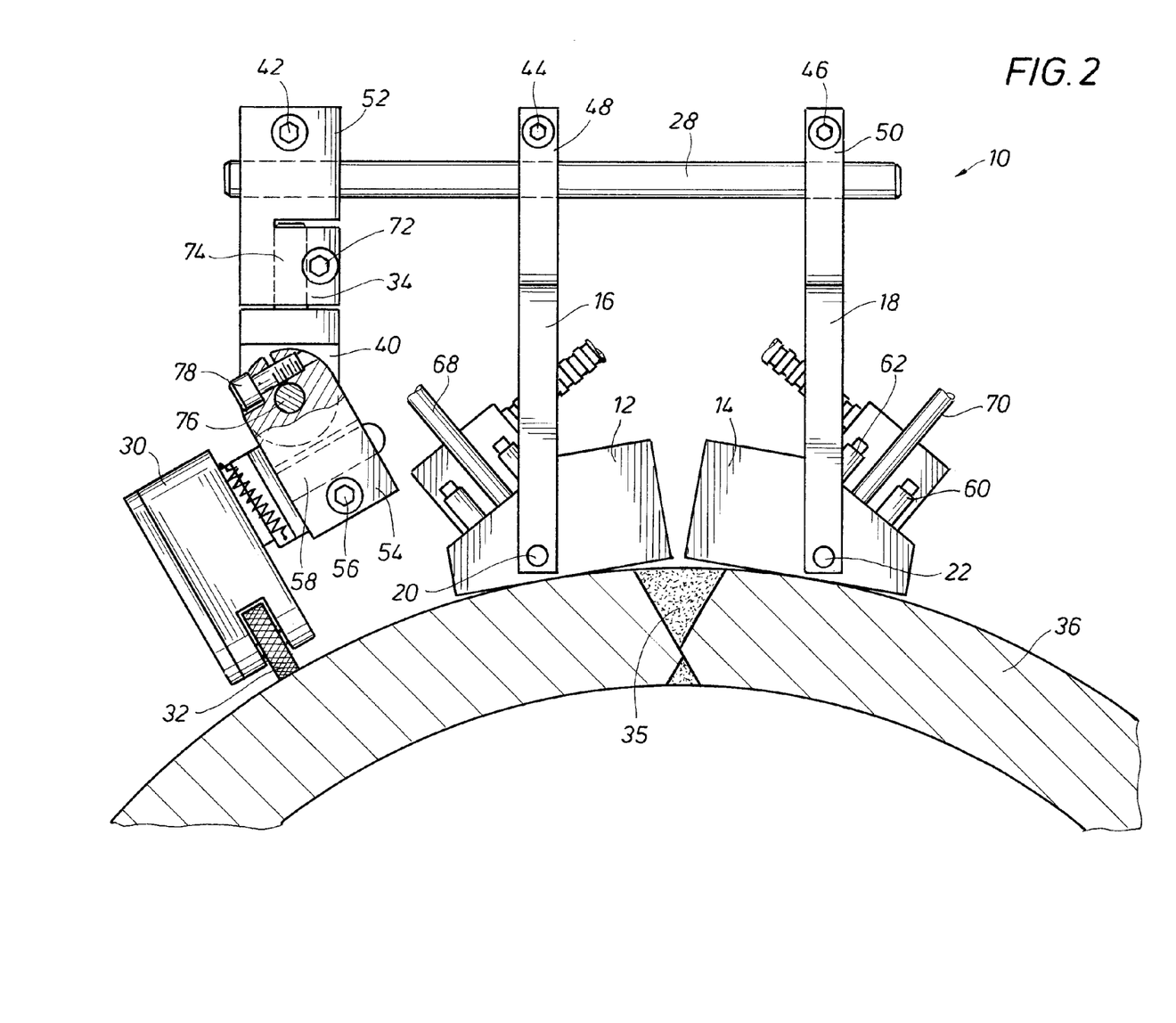
FIG. 2 is an elevational view, partially in section, that illustrates an acoustic scanner frame for use in scanning a weld in accord with one possible embodiment of the invention.

In one embodiment, wheel 32 may tilt utilizing tilt pivot 40, best shown in FIG. 2, for rotation in a different axis of rotation. In FIG. 2, the axis of rotation for pivotal movement of wheel 32 is around the axis of shaft 76. The desired pivotal position can be secured by tightening nut 78. Wheel pivot connection 34 may comprise tightening/loosening nut 72 and corresponding shaft 74.

Accordingly, encoder mechanism 30 may be utilized to record a position in more than one direction as compared to the orientation of support 10 utilizing only one wheel 32. In the embodiment of FIG. 2, encoder tilt pivot 40 is provided to permit encoder wheel 32 to be oriented in virtually any desired position. For example, encoder wheel 32 may be oriented to measure movement of the sensors for different types of structures and surfaces, e.g., for the curvature of pipe 36 and/or different orientations of welds. In FIG. 1, surface 38 might be the surface of a large pipe, a flat surface, a tank, some other surface comprising a weld or possible corrosion, a relatively small pipe with a weld transverse to the axis of the pipe, and/or any other desired materials to be scanned. Accordingly, in one possible embodiment of the present invention, the present invention may be utilized to verify a wide range of different types of welds, which may comprise welds of threaded portions to large diameter pipes.

The distance between wheel 32 and transducers (signal sources) 12 and 14 may be adjusted utilizing clamp 52 and/or clamp 54. Clamp 52 may be used to adjust encoder mechanism 30 along module shaft 28. Clamp 54 may be used to adjust a rotational or tilt position of wheel 32 using nut 56 and, if desired, to adjust a relative position of shaft 58.

Figure 5:
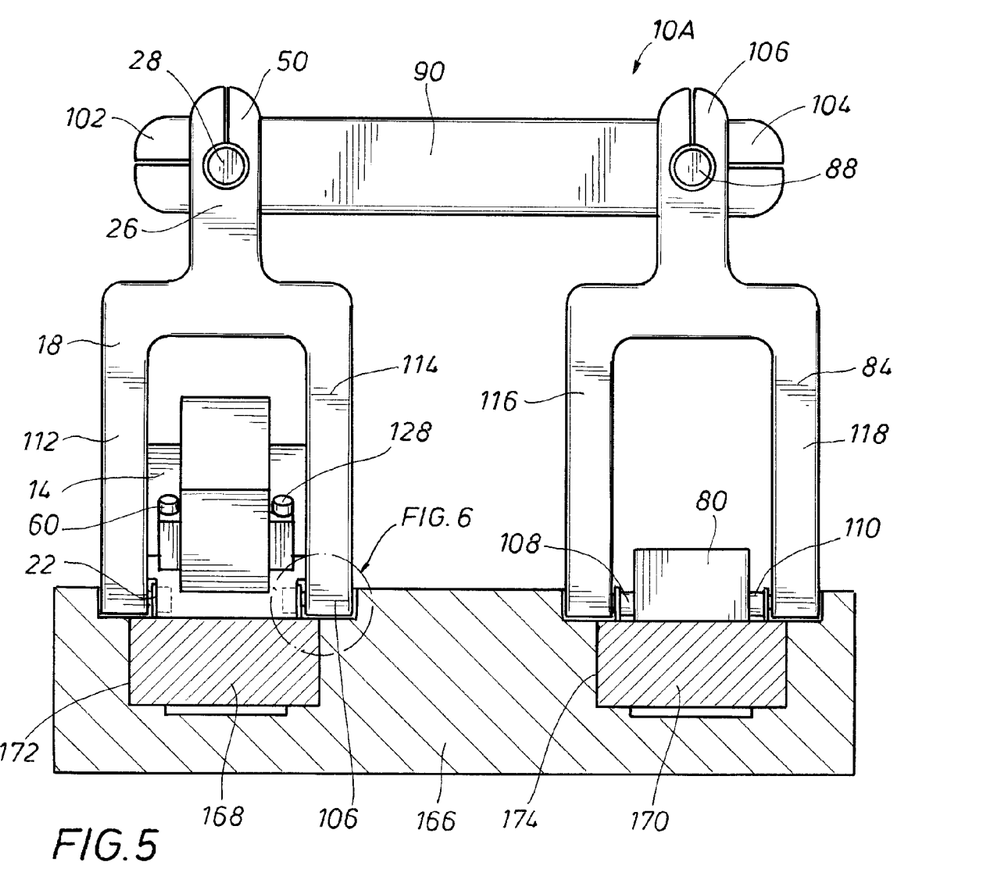
FIG. 5 is a cross-sectional view, partially in section, along lines 5-5 of FIG. 4, that illustrates the possibility of multiple acoustic sensors linked by a modular acoustic scanner frame for calibration within multiple slots defined within a calibration block that may be utilized for simultaneously calibrating multiple acoustic sensors which may or may not be of various types, in accord with one possible embodiment of the invention.

Referring to FIG. 1 and FIG. 5, the phased array transducer offset adjustments 60, 62, and 128 may be provided as part of a phased array transducer to prevent wear on the bottom of the transducer by adjusting the offset between the material to be investigated and the bottom of the phased array transducer. Adjustments 60, 62 and 128 and/or other types of transducer position adjustments may be utilized on other transducers.

Cables 64 and 66, shown in FIG. 1, and/or other electrical cables or lines may also be supported utilizing support frame 10. Fluid lines 68 and 70 may be utilized to pump water or other suitable types of acoustic couplant between the acoustic transducers (signal sources) and the material to be inspected. Water is often used as an acoustic couplant.

Figure 4:
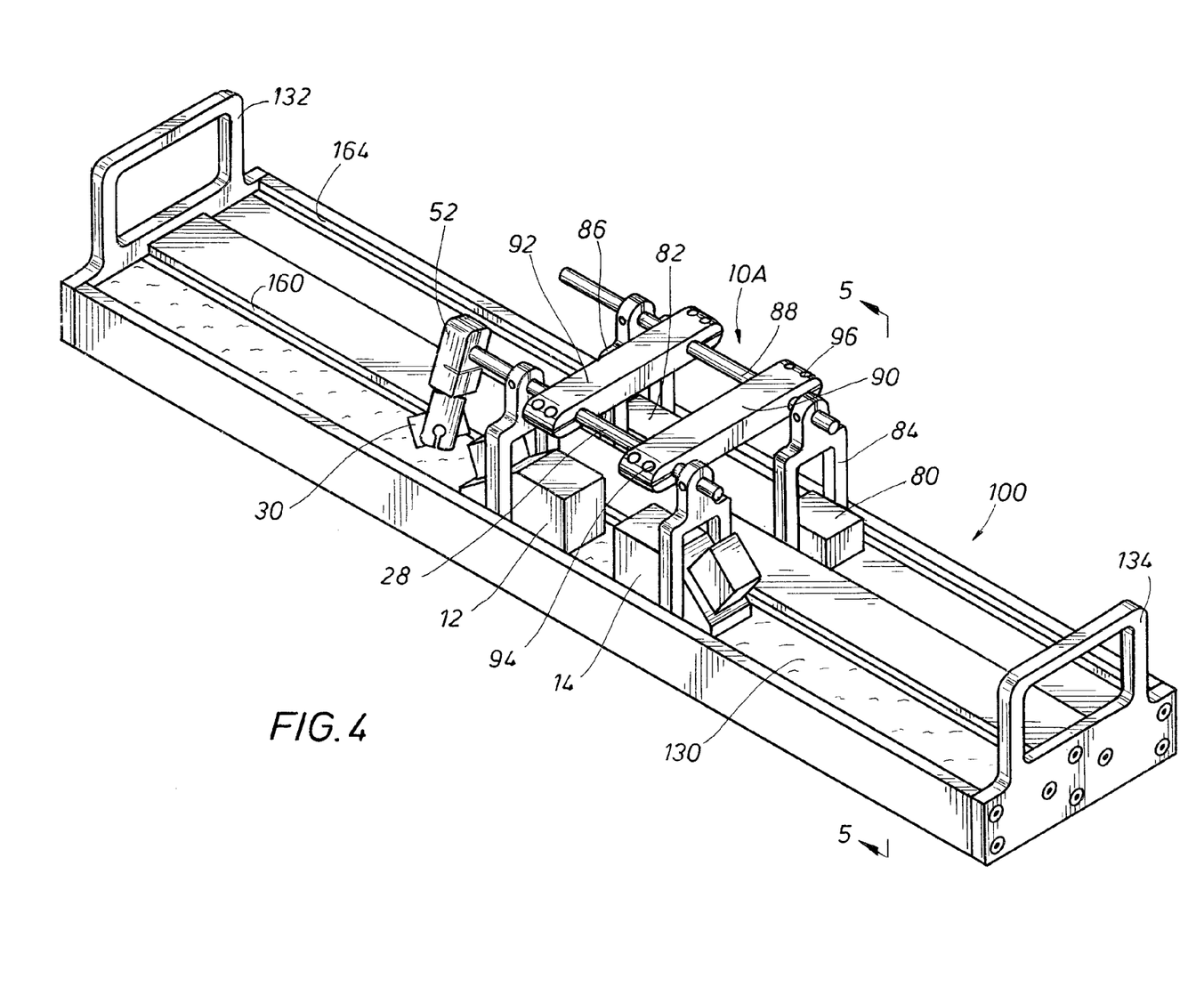
FIG. 4 is a perspective view of an acoustic scanner frame with a first modular link for use with a calibration block embodiment that may be utilized for simultaneously calibrating multiple acoustic sensors of various types in accord with one possible embodiment of the invention.

FIGS. 3 and 4 show support frame embodiments 10 and 10A as they may be used within one possible embodiment of calibration block 100. In FIG. 4, shaft interconnection members such as link members 90 and 92 may be utilized to add an additional module comprising additional forks 84 and 86 to support additional transducers (signal sources) 80 and 82. Link members 90 and 92 interconnect module shaft 28 and additional module shaft 88. It will be appreciated that any number of link members may be used to interconnect any number of different modules, such as additional phased array acoustic transducers, time of flight acoustic transducers, and other types of transducers. In one preferred embodiment, different sets of link members are utilized to add each additional module. However, in another embodiment, each of the link members might comprise multiple internal clamps or holes for additional module shafts besides module shaft 28 and additional module shaft 88. Fasteners, such as sets of nuts indicated by numerals 94 and 96, on either end of link member 90 may be utilized to clamp or release module shaft 28 and additional module shaft 88.

FIG. 5 shows additional enlarged details of support frame 10A looking into the cross-sectional line 5-5 of FIG. 4. As also shown in FIG. 4, link member 90 interconnects module shaft 28 and additional module shaft 88. Link member 90 may comprise link member clamp 102 at one end of link member 90 and link member clamp 104 at the opposite end thereof. As discussed hereinbefore, link member clamps 102 and 104 may be formed integrally with link member 90. Link member clamps 102 and 104 may be tightened or loosened for insertion or removal of module shaft 28 and additional module shaft 88, respectively. Integral fork end clamps 50 and 106 connect the respective forks 18 and 84 to corresponding module shafts 28 and 88. As discussed hereinbefore, the use of similar integral clamps on the various components provides for simple construction and interchangeable fasteners for tightening/loosening the clamps.

Although not shown, link members 90 and 92 may also comprise an adjustable extension shaft or member, if desired.

If desired, forks 18 and 84, and/or other forks may be identical. As indicated in FIG. 5, each fork prong 112, 114, 116, and 118 may be substantially the same or mirror images. However, this same or similar sized fork may be utilized to support different size transducers. For instance, as shown in FIG. 5, phased array transducer 14 is substantially larger than transducer 80, which might be a time of flight acoustic transducer. The term "fork prong" as used herein provides a distinctive terminology for this component for help in describing an embodiment of the invention, but is not intended to limit the construction to that shown, and should be understood to include various constructions of legs, extensions, rods, members, and the like.

Figure 6:
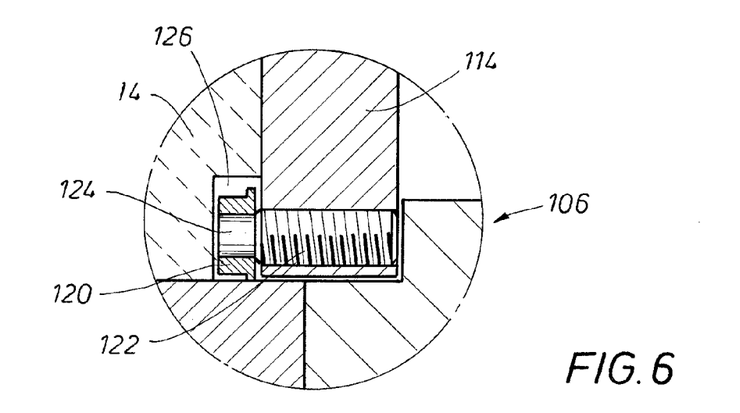
FIG. 6 is an enlarged elevational view, partially in section, that illustrates details of a pivotal mounting that may be utilized for securing different size transducers, or different types of transducers, and different numbers of transducers, utilizing substantially identical components such as forks and links to form a scanner transducer support frame in accord with one possible embodiment of the invention.

Variable size or length pivot assemblies 22, 106, 108 and 110 shown in FIG. 5 may be utilized to interconnect different sized transducers (signal sources) utilizing the same size forks. Referring to the enlargement of pivot assembly 106 as illustrated in FIG. 6, pivot element 120 may be secured to fork prong 114 utilizing threaded member 122. Threaded member 122 may also comprise shaft 124, which may be pressed to fit into or rotatable with respect to pivot element 120. Pivot element 120 may be inserted into openings formed in the transducers, such as pivot receptacle 126. As noted previously, the offset of a standard acoustic transducer from the material to be investigated may be adjusted using offset adjustment 60 and/or other offset adjustment members such as offset adjustment 128. Therefore, pivot receptacle 126 may provide sufficient space to permit such offset adjustments. The axial length of the pivot elements may vary to compensate for different size transducers. Alternatively, threaded member 122 may be adjusted to position a common sized pivot element 120 into pivot receptacle on the bodies of different sized transducers.

Referring now to FIGS. 3 through 14, there are shown various features of modular calibration block 100 that may be utilized for calibrating many transducers (signal sources) simultaneously and/or as they are simultaneously moved. In a preferred embodiment, the advantages of support frame 10 or support frame 10A may be used in conjunction with the advantages of calibration block 100 for enhanced calibration. However, it will be understood that the concepts, features, advantages, and methods of calibration block 100 may be enjoyed separately from use of support frame 10 and/or support frame 10A. Moreover, support frame 10 and embodiments thereof may be used separately from calibration block 100.

Figure 7:
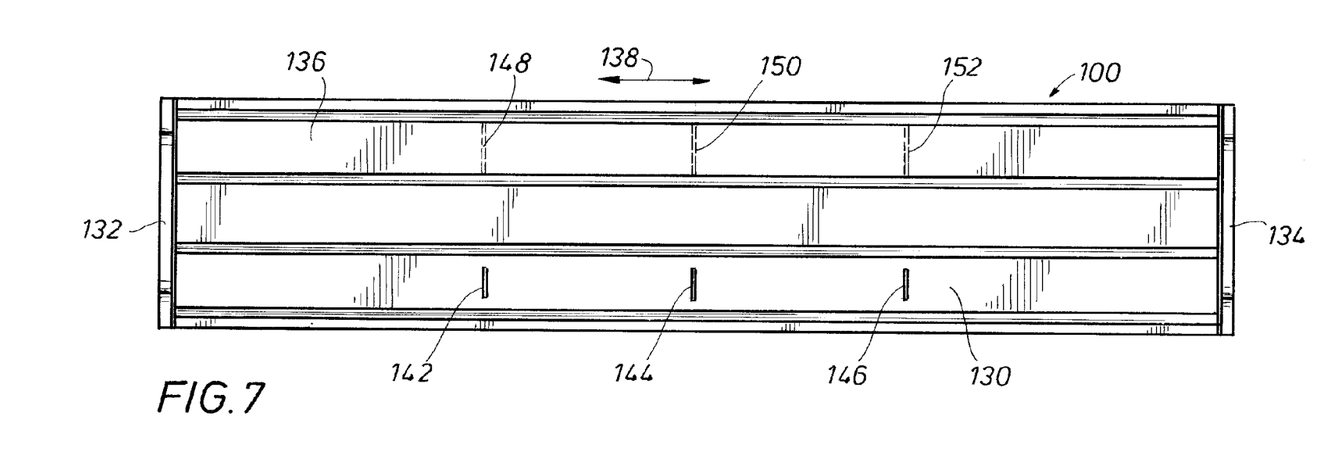
FIG. 7 is a top view, partially in section, illustrating construction details of a modular calibration block that may be used for calibration of multiple acoustic transducers, which transducers may or may not be of different types, in accord with one possible embodiment of the invention.

As perhaps best shown in FIG. 7, calibration block 100 may comprise various calibration features, "errors," or "imperfections" embedded therein at various positions. The calibration features may or may not be standardized features that are utilized generally for calibrating acoustic transducers (signal sources) and/or other types of transducers.

In one possible preferred embodiment, calibration block 100 may comprise at least one elongate calibration path 130 that, in this embodiment, may extend from handle 132 to handle 134. The embodiment of calibration block 100 shown in FIGS. 3 through 14 also comprises a second elongate calibration path 136. Multiple elongate calibration paths permit simultaneous calibration of multiple modules of transducers. For example, the transducers (signal sources) may be simultaneously moved along calibration paths 130 and 136 by movement of support frame 10. The movement may be continuous and/or in stages. Data produced by the transducers (signal sources) may be recorded with respect to position during this movement. The data may be combined and compared with the expected results to verify that the calibration is good. The interaction between engagements surfaces on support frame 10 with engagements surfaces on calibration block 100 reliably position the transducers (signal sources) with respect to the calibration features to enhance repeatability of the calibrations.

The present invention may comprise any number of calibration paths which may be incorporated into a single calibration block or which may be provided in multiple calibration blocks laid side to side. If multiple calibration blocks are utilized, then interconnection means may be provided to secure the blocks together, if desired. Calibration features, which may comprise features or "defects" of a known geometry, are embedded in calibration paths 130 and 136 as indicated at 142, 144, 146, 148, 150, and 152.

The transducers (signal sources) to be calibrated may be moved simultaneously up and down the calibration paths as indicated by direction of movement arrow 138 in FIG. 7. As discussed above, the movement of support frame 10 in this direction is transverse or perpendicular to the direction of movement of support frame 10 in FIGS. 1 and 2 along weld 35. Because the calibration data may be recorded with respect to position, the direction of movement of support frame 10 is not important. As discussed hereinbefore, encoder wheel 32 may be oriented to move linear with or parallel to center portion 140 in the same direction as indicated by movement arrow 138. In one preferred embodiment, each calibration path is recessed as shown in FIGS. 3 and 4. These recesses may be watertight to form water traps and thereby eliminate the need to circulate or supply acoustic couplant fluids such as water. This reduces the complexity of calibrating and provides that the flow of water couplant is not a variable factor.

Figures 10, 11, 12:
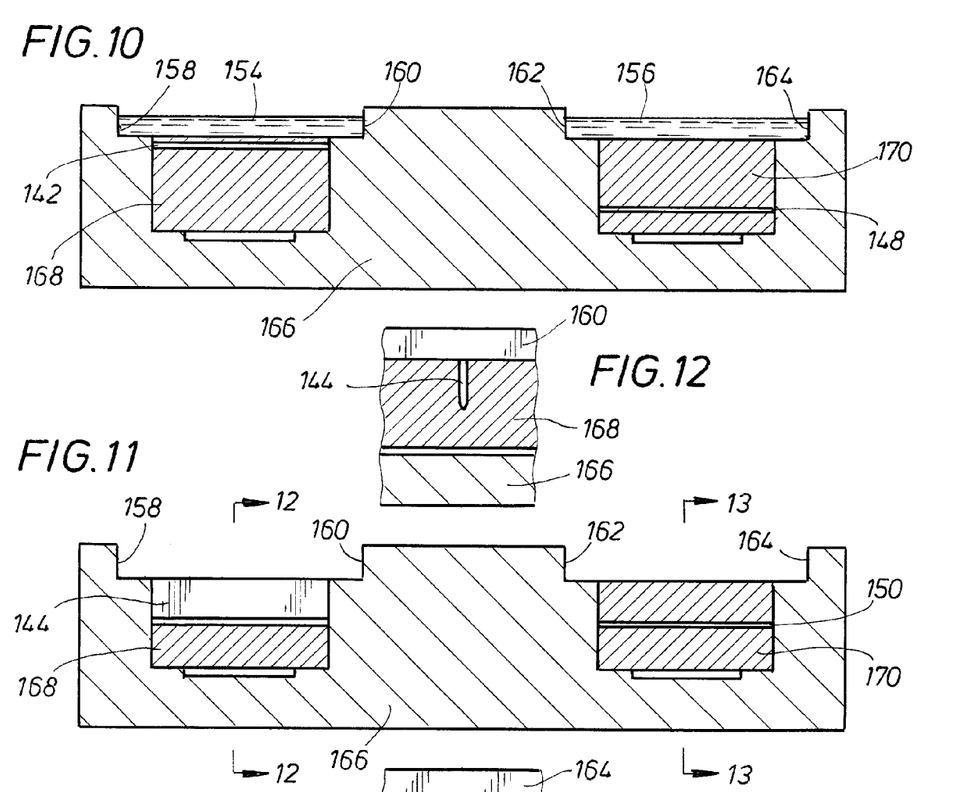
FIG. 10 is a cross-sectional view, along lines 10-10 of FIG. 9, of a modular calibration block illustrating cross-sectional views of potential imbedded calibration features or "errors" of known dimensions that may be used for calibration of multiple acoustic transducers, in accord with one possible embodiment of the invention.
FIG. 11 is a cross-sectional view, along lines 11-11 of FIG. 9, of a modular calibration block illustrating other cross-sectional views of imbedded calibration features of known dimensions that may be used for calibration of multiple acoustic transducers, which transducers may or may not be of different types, in accord with one possible embodiment of the invention.
FIG. 12 is a cross-sectional view, along lines 12-12 of FIG. 11, of a modular calibration block that illustrates a side view of the imbedded calibration features shown in FIG. 11 that may be used for calibration of multiple acoustic transducers, in accord with one possible embodiment of the invention.

Accordingly, these water traps may create a pool of water as indicated by pools 154 and 156 shown in FIG. 10.

Figures 13, 14:
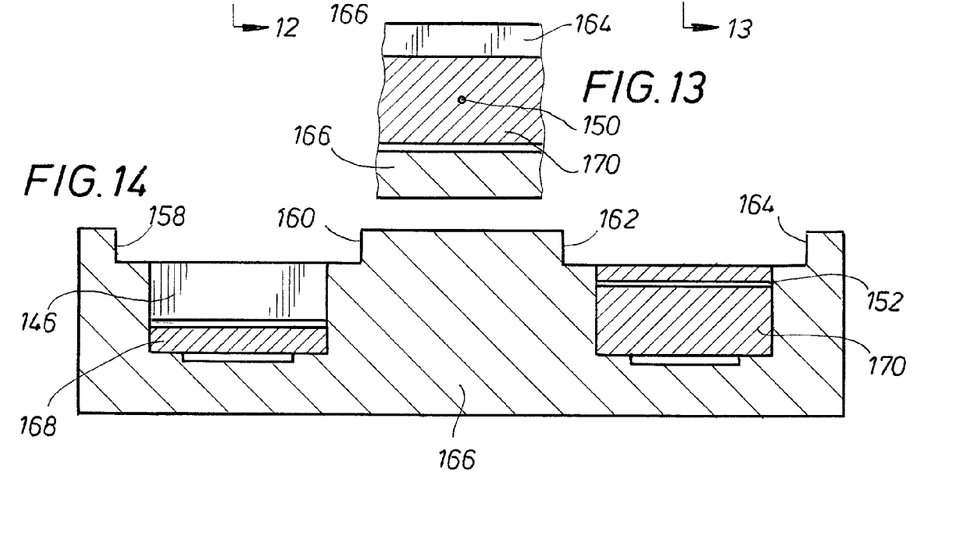
FIG. 13 is a cross-sectional view, along lines 13-13 of FIG. 11, of a calibration block that illustrates a side view of the imbedded calibration feature of FIG. 11 that may be used for simultaneous calibration of multiple acoustic transducers, in accord with one possible embodiment of the invention.
FIG. 14 is a cross-sectional view, along lines 14-14 of FIG. 9, of a modular calibration block that illustrates additional imbedded calibration features of known dimensions that may be used for calibration of multiple acoustic transducers, which transducers may or may not be of different types, in accord with one possible embodiment of the invention.

Pools 154 and 156 may be defined by guide members such as guide walls 158, 160, 162, and 164, as best shown in FIGS. 10, 11, and 14. Other types of guide members or walls may be utilized to define pools, which contain fluid couplant.

Guide members, such as guide walls 158, 160, 162, and 164, may provide an additional function because they are preferably sized to fit closely with the forks such as forks 18 and 84 shown in FIG. 5. The close fit of the forks within the guide walls constrains the simultaneous movement of the transducers (signal sources) along a particular path and therefore provides highly repeatable physical movements that improve the repeatability of the calibrations. In one embodiment, the sides of prongs 116 and 118 provide square mating surfaces that engage the guide walls thereby preventing rotation of the acoustic transducers (signal sources) during calibration. As discussed above, although specific prongs are disclosed in the drawings, prongs 116 and 118 are intended to comprise any suitable structures such as extensions, arms, members, or the like, to support the transducers.

Thus, in one possible embodiment, guide members or guide walls 158, 160, 162, and 164 constrain the position or orientation of the transducers. The guide members may also cooperate with support frame 10 or 10A to perform this function. Other types of guide members may be utilized to guide or orient or position acoustic transducers (signal sources) such as clamps, rails, alignment rods for alignment holes, fasteners, sockets, walls, stop surfaces, alignment ridges or openings or cooperating members, and the like, and/or combinations of such guide members. The guide members may be utilized to orient and/or position and/or space the transducers (signal sources) with respect to known defects or features for calibration purposes.

Thus, the guide walls comprise engagement surfaces that may perform multiple functions such as retaining acoustic couplant and/or constraining movement of the transducers (signal sources) along a highly repeatable path. While particular guide walls are illustrated here, it will be appreciated that the guide walls may be of many different configurations. In general, the guide walls may comprise respective engagement surfaces for positioning the acoustic transducers (signal sources) at a known position or along a known path on or along or within calibration block 100.

Figures 8, 9:
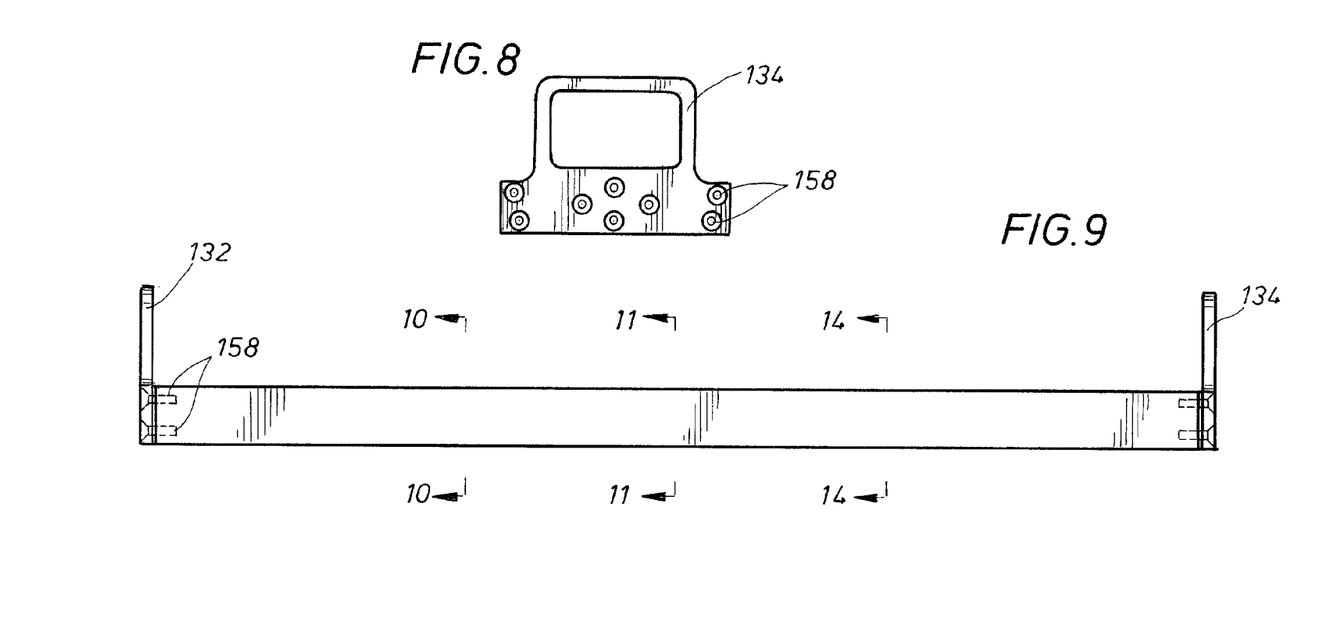
FIG. 8 is an elevational end view illustrating construction details of a modular calibration block for use in calibrating multiple acoustic transducers, in accord with one possible embodiment of the invention.
FIG. 9 is an elevational side view, partially in section, illustrating construction details of a modular calibration block that may be used for calibration of multiple acoustic transducers, in accord with one possible embodiment of the invention.

The components of calibration block 100 may be held together by fasteners, such as fasteners 158 indicated in FIGS. 8 and 9. Therefore, in one possible embodiment, the components of calibration block 100 may be easily connected and disconnected, as desired. Components of calibration block 100 may comprise handles 132 and 134 shown for instance, in FIGS. 3 and 4. The handles may be utilized for lifting purposes but may also be utilized as end pieces that secure internal calibration members 168 and 170 within calibrator frame 166.

In one embodiment, calibration members 168 and 170 may be machined as one-piece blocks that fit closely within calibrator frame 166, as shown in FIG. 5. Calibrator frame 166 may comprise elongate slots or receptacles 172 and 174 that are machined to provide the close fit with calibration members 168 and 170 and to define calibration paths 130 and 136. Calibrator frame 166 may also be of one piece or integral construction. Calibrator frame 166 may comprise one or more elongate receptacles, but in this embodiment comprises two receptacles. Calibration members 168 and 170 may be machined with a rectangular cross-section as shown, but could comprise other cross-sections whereby receptacles 172 and 174 comprise mating profiles to provide a secure and tight fit. Their length is machined to fit tightly at the ends to be secured by handles 132 and 134. The components of calibration block 100 may be comprised of suitable metals such as steel, and the like. Calibration members 168 and 170 may or may not be of the same material. Likewise, calibrator frame 166 may or may not be of the same material as calibration members 168 and 170.

It will be appreciated that the secure fit of the calibration block components prevents variations in calibrations. It will be appreciated that the general calibration process involves collecting data from the sensors wherein the calibration structures are predetermined. A correct calibration should then have a predetermined result that can be verified and repeated.

Cross-sectional views indicated in FIG. 9 cut through calibration features 142, 144, 146, 148, 150, and 152 as shown in FIG. 7. FIGS. 10, 11, and 14 show the cross sectional views of the calibration features, which are embedded into calibration members 168 and 170. The calibration features shown here are intended to be representative of possible calibration structures, but are not intended in any way to be limited to the structures that are shown.

Referring to FIG. 10, calibration feature or "defect" 142 may comprise for example, a relatively shallow slot machined into member 168 at a particular axial position along calibration path 132, as shown in FIG. 7. Referring to FIG. 11, calibration feature or "defect" 144 may comprise for example, a medium depth slot. FIG. 12 shows a cross-sectional view of calibration feature 144. Calibration features 142, 144, and 146 may have different depths but have the same width. In FIG. 14, calibration feature 146 may comprise a relatively deep slot.

Calibration features 148, 150, and 152, are machined into calibration member 170, as indicated in FIGS. 10, 11, 13, and 14. In this example, the calibration feature is a hole positioned at different depths. In this example, the hole has an axis parallel to the bottom of the calibrator frame 166 and extending from one side to the other of calibration member 170. In FIG. 10, the hole is at a relatively deep position. In FIGS. 11 and 14, the hole is at a medium depth and a shallow depth, respectively. FIG. 13 shows a cross-sectional view of the medium depth calibration feature 150.

In one possible mode of operation of calibration block 100, transducer support frame 10, 10A, or some other support frame may be moved along the elongate calibration paths 130 and 136 either continuously or in stations. Movement of the transducer support moves any number of transducers (signal sources) simultaneously. Encoder wheel 32 may be pivoted to a position to ride along center portion 140 so that the position of the transducer support frame is known. As explained hereinbefore, the physical path or position(s) taken by the transducers (signal sources) with respect to the calibration features, in accord with one possible embodiment of the invention, is constrained to be identical each time a calibration is taken. The calibration data can then be recorded for all transducers (signal sources) at each station and/or continuously along my calibration path as proof of the calibration. The calibration data can be viewed to see the known features or "defects" 142, 144, 146 and 148, 150, and 152 embedded in calibration members 168 and 170. For this purpose, it may be desirable to combine or overlay the data to create a calibration picture that can be visually compared with an expected calibration picture. The calibration may also be electronically verified by software comparison, if desired.

In one example, because data from multiple transducers (signal sources) may be recorded simultaneously for calibration purposes, and/or if the multiple transducers (signal sources) are moved simultaneously with support frame 10, then it is submitted that the multiple transducers (signal sources) are simultaneously calibrating. In one embodiment, calibration may be referred to as simultaneous if the calibrations are made in a single pass or a limited number of passes. The calibrations may be said to be simultaneous even if the signals from the transducers (signal sources) are multiplexed in some manner and may not occur exactly at the same electronic moment in time. It is not always necessary or practical that the readings be taken at "simultaneous moments" with respect to atomic precision measurement limitations and generally if a sufficient number of samples are taken over a region for each transducer (signal source) then the calibration is simultaneous. Digital sampling rather than recording of analog signals can both be used for obtaining simultaneous calibrations. Generally, as used herein, when the same position data from encoder 30 is obtained by movement and/or positioning of all sensors with the same frame 10 or 10A or other frame, then the calibrations might be considered to have been made simultaneously to multiple transducers (signal sources). As well, if multiple sensors (signal sources) are placed or fixed in various positions on the calibration block so that readings may be taken prior to movement, then the calibration involves simultaneous calibration of multiple transducers.

Simultaneous calibrations may be utilized to improve the reliability and time required for calibration by verifying that all transducers (signal sources) cooperate with each other. Assuming the calibration data from all transducers (signal sources) simultaneously calibrated is correct, then the views of the known "defects" will be the same from one calibration to another. Moreover, when the data is merged together, when transducers (signal sources) are cooperating correctly as can only occur when the transducers (signal sources) are properly calibrated, an overall or merged view is visible that is repeatable. During the calibration procedure, it can be verified that the transducers (signal sources) are oriented correctly because the data from the different transducers (signal sources) should match or be combined in a manner that produces a consistent and accurate view of the known "defects."

After calibration, the transducers (signal sources) support frame may be taken directly from calibration block 100 and placed on the material to be investigated without the need to alter or change the mounting of the transducers. Because all the transducers (signal sources) were calibrated simultaneously while being mounted in the same frame that will subsequently be used for examination of the material to be investigated, an operator can have high confidence that the calibrations have not changed due to minor variations in the orientation of the transducers (signal sources) from one operation to the next.

The water traps for pools 154 and 156, defined within one possible embodiment of calibrator 100, provides a consistent supply of acoustic couplant from one calibration to the next. In one embodiment of the invention, as discussed above, the guide walls that define the pools are designed to mesh with the flat sides of the prongs of the forks, thereby constraining the position of the transducers (signal sources) for consistency from one calibration to the next.

The features of the calibration block and/or support discussed hereinbefore provide a much quicker and more accurate calibration, which may only require minutes, as is highly advantageous for providing feedback which prevents expensive welding errors and improves welding accuracy.

Using features discussed herein, the present invention provides a highly accurate calibration that may be used to calibrate multiple detectors with a single pass or scanning pass. The accuracy of the present invention allows for simultaneously calibrating even a plurality of highly sensitive phase detector acoustic transducers and verifying that the phase detectors are cooperating with each other. However, if desired for any reason, additional scanning passes might be used, e.g., such as for providing averaging of signals, calibration pictures, and the like. Additional scanning passes may not be necessary due to the high accuracy calibration of the present invention.

To limit the scanning time to provide more instantaneous feedback, such as may be desired in welding verification operation, in one possible embodiment, the number of scanning passes may be limited to between one and five scanning passes.

In a scanning pass, the plurality of acoustic transducers and/or position sensors are moved with respect to the plurality of known calibration features. The calibration scanning pass may be made prior to said scanning of said material to be investigated, such as at the beginning of a shift for welding pipe. The calibration scanning pass may be made by moving the support frame and the plurality of acoustic transducers with respect to the plurality calibration features in a desired direction, and perhaps from a designated starting point to a designated ending point. In one embodiment, the plurality of acoustic transducers may be moved along a straight path, which may be predefined and easily repeatable, as discussed herein. During the scanning pass, information is recorded such as, for example, the position information from the encoder or other position sensor(s) and/or respective outputs of the plurality of acoustic transducers (signal sources) in response to the calibration features.

In one embodiment, after data is received from a scan or traverse of the elongate calibration paths, the data for the transducers (signal sources) in a particular elongate calibration path can be overlaid. This will produce a known picture from calibration to calibration. Viewing the combined picture will show that the "defects" are the proper size, and depth, and when combined to create a 2-D or 3-D picture, the "defects" are not improperly enlarged on one side or the other, when the defects comprise a uniform geometry. This picture proves that the transducers are accurately aligned with each other and cooperating with each other. Accordingly, as described above, different types of transducers (signal sources) such as phased array acoustic transducers (signal sources) and time of flight transducers (signal sources) may be calibrated simultaneously with the results checked to verify the transducers (signal sources) read consistently with respect to each other.

Support frame 10 is modular in construction and permits multiple transducers (signal sources) to be mounted within interconnected forks. The forks permit the transducers (signal sources) to pivot in least one degree of freedom to conform to the surfaces of the material being investigated. Pivot assemblies, such as pivot assembly 106, work in conjunction with offset adjustments that are often provided to protect the surface of acoustic transducers. Axial spacing between the transducers (signal sources) is easily adjusted by use of integral clamps that may be used throughout support frame 10 to provide a wide range of adjustments.

In one embodiment for use in automatic machines for welding large diameter tubulars, it has been found that calibration of prior art phased array scanners may frequently require two or more hours. On the other hand, in accord with various embodiments of the present invention, a calibration of a phased array acoustic scanner for inspection of a weld may be accomplished in approximately fifteen minutes. This is especially useful when welding threaded ends to large diameter tubulars, because it is desirable or may even be required that calibrations be repeated at least once per shift. Because the present invention provides a calibration system that may be utilized to significantly reduce the time of calibration, the calibration system/method of the present invention may be utilized to provide a huge boost to productivity for use with large diameter tubular welding machines.

As one possible example, a large diameter welding machine for making end welds on large diameter tubulars may produce a weld every twenty-five minutes. For a more specific example, a typical 20" OD×0.625" wall pipe may be welded to an end portion in twenty-five minutes. If a selected embodiment of the phased array weld verification method takes only fifteen minutes, then the resulting phased array weld verification system is up and running before the first weld comes off the line. Otherwise, as with prior art phased array weld verification systems, production is held up on the initial (first article) weld some ninety-five minutes (one hundred twenty minute calibration time minus twenty-five minute weld time), at the start of each shift and at other times when a new calibration is required.

Embodiments of the present invention may also produce a scan of the weld for large diameter pipe very quickly. One possible scanner configuration allows making a phased array weld verification scan in only one minute (on typical 20" OD×0.625" wall pipe). For this type of operation, this is effectively a "real time" or near real time scan because the scan time is relatively low as compared to the weld time for each weld.

In this case, the weld time versus scan time is 25:1. Without the "instant" feedback, the large diameter pipe welding machine may quickly lose its own calibration and start producing defective welds due to variations in heat input, wire feed rate, welding speed, and/or other adjustable factors. At twenty-five minutes per weld, a weld machine for large diameter pipes can soon fill a rack with bad pipes—which results in expensive losses. The high speed of the weld inspection system of the present invention may be utilized to prevent that from happening. Because the scan time is so much less than the weld time, the inspection system of the present invention effectively gives "eyes" to the machine operator and helps him continually adjust his heat input, wire feed rate, welding speed and other important, adjustable factors to keep the machine producing defect free welds.

Even with a scan rate of five minutes, whereby the weld time versus scan time is 5:1, the present invention is highly advantageous. With a phased array weld inspection system in accord with the present invention, it has become possible to produce hundreds of defect free welds in a row. With the same large diameter pipe welding machine, rejection rates may be as high as 40%, or possibly more without the use of real time or near real time inspection as per the present invention. It will be appreciated that prior art attempts to produce automatic systems for welding large diameter pipes have failed to be economical.

As noted above, calibration blocks with a side-drilled hole, a notch, or other internal reflector for velocity, amplitude, and wedge delay are well known, but have not been helpful in solving the many problems for calibrating phased array sensors and/or other sensors as discussed hereinbefore.

However, various features of possible embodiments of the invention, as discussed above, uniquely address the above and/or other problems with solutions and/or benefits. In one embodiment, such features include means for locking or securing the probes into the calibration block to ensure there is limited or no appreciable undesired movement of the sensor, e.g. the phased transducers (signal sources) are precisely/repeatably/reliably aligned for each calibration. For example, in one possible embodiment, guide walls 158, 160, 162, and 164 may cooperate with transducers (signal sources) and/or transducer frames such as forks 16, 18, 84 and 86 to lock the transducers (signal sources) into axial alignment. Thus, the transducers (signal sources) are constrained to move in an identical path or to be positioned/oriented identically for each calibration. In one embodiment, the calibration may require movement of the phased array sensors along a path which may comprise various calibration features such as along elongate calibration path 130 or 136, or the like. In another embodiment, the transducers (signal sources) might be locked as desired at specific stations in a precise orientation/spacing with respect to one or more calibration features or known defects.

As discussed above, possible embodiments of a calibration block in accord with the present invention may comprise one or more fluid containment regions built into the housing such as pools 154 and 156 or the like, which may be designed to contain liquid acoustic couplant, so that there is no need to provide a constant stream of water or use a viscous substitute (which does not produce repeatable results).

In other possible embodiments of the present invention, the calibration "housing," such as calibrator frame 166, may be utilized to modularly hold multiple calibration blocks together in order to calibrate different types of probes or use different calibration methods on the same kinds of probes at the same time. Internal calibration members 168 and 170 and/or additional and/or replaceable calibration members may comprise part of calibrator 100 and/or be utilized and/or replaced as desired.

In other possible embodiments of the present invention, enough distance or spacing is provided between the defects to facilitate the "sweep" calibration (calibrating to ensure that all angles see the same defect in the same position and amplitude), even when this sweep covers such a wide variety of angles and distances along that angle. In one possible embodiment, which may vary depending on the types of scanners utilized, the spacing or distance between defects may be five to ten or more inches apart.

In one possible embodiment, a relatively long spacing coupled with a relatively thin internal calibration member, e.g. 168 and 170, enables one to see the same defect with multiple angles and "legs" from the same position at the same time. In one possible embodiment, if internal calibration member is approximately one inch, then the ratio of defect spacing to calibration member width of approximately one inch or so may produce a ratio of 5:1 to 10:1 or greater.

In another embodiment, a calibration housing may be provided that enables the encoder to be turned 90 degrees to permit a scan along the block utilizing multiple phased array sensors and/or other acoustic sensors, whereby the data for each sensor made during this movement of the encoder can be correlated with respect to distance based on the encoder, so that a simultaneous "merge view" of the calibration block or blocks can be produced. This merge view can be compared with a predetermined merge view to verify that all transducers (signal sources) are calibrated and operating as desired. With the merged view of data from multiple acoustic transducers, which may in some cases be adjusted using position data so that all views might be seen from a particular position, one can quickly see that all of the different angles and probes "stack" or align so that a given defect produces data from each sensor that is correctly in the same position and depth and with the same amplitude. Therefore, the calibration block of the present invention may be utilized with the rotated encoder transducer to allow one to record this information in totality. Accordingly, the present invention may be utilized to provide unmatched comparison and verification of calibration results over the full range of probes, depths, and angles being used.

This level of comparison for a "merge view" provides unsurpassed accuracy for the fine adjustment of the set screws in the wedges and checking for probe wear. In one embodiment, with a single calibration scan that takes approximately 10 seconds, one can verify the detectability of a certain size defect, defect position, defect amplitude, orientation and spacing of probes in relationship to each other, and that the encoder reports the correct distance traveled. By providing for a place where the encoder can roll along the block, such as raised center portion 140 that permits encoder usage for making a "block" scan, simultaneously produced scans from multiple transducers (signal sources) may be overlaid as discussed hereinbefore.

In another embodiment, handles 132 and 134 may be provided for more easily transporting the calibration block, which may typically be quite heavy for lifting by an individual or two-man team. This feature may be especially useful when calibrations may be required at different locations. For example, it may be necessary to provide a calibration on a reactor vessel in a refinery perhaps a hundred feet in the air on scaffolding. Elevators are normally unavailable for this type of operation. The instruments, probes, computer, and the like may need to be transported while wearing full safety gear with fall arrest harness. The handles 132 and 134 are also part of a frame and end stop that limits movement of the acoustic transducers.

In yet another embodiment, a scanner frame may be provided that is rigid, simple/reliable in operation, light, adjustable, and highly configurable. As noted above, transducer support frame 10, 10A, and component variations as discussed hereinbefore, may be designed to cooperate or engage with transducer orientation features such as guide members formed in the calibration block to produce consistent, reliable, quick calibrations. It will be appreciated and has been mentioned previously that embodiments of the present invention may utilize different thicknesses, different spacing between blocks, and other variations. As one possible non-limiting, one to five calibration members, such as members 168 or 170 or other calibration members with defects, might be utilized side by side instead of two, as shown for purposes of example in the drawings.

It will be understood, that the drawings included herewith are intended to describe the concepts of the invention so that the presently preferred embodiments of the invention will be plainly disclosed to one of skill in the art but are not intended to be renditions of finalized product designs and may include simplified conceptual views as desired for easier and quicker understanding or explanation of the invention. For instance, if desired to move support frame 10 in the same direction of the weld, then calibration block 100 might be modified so that the calibration features are provided in center portion 140 and support frame 10 supports transducers (signal sources) 12 and 14, or other transducers, on opposite sides of center portion 140, and with alternative guide surfaces to constrain the movement. While the invention has been described in connection with one or more possible embodiments, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A method for calibrating a plurality of acoustic transducers prior to or after scanning a material to be investigated, comprising:
   providing that said plurality of acoustic transducers are mounted to a support frame for simultaneous movement therewith;
   providing a calibration block comprising a plurality of known features;
   positioning said support frame and said plurality of acoustic transducers against said calibration block;
   making fewer than six scanning passes of said plurality of acoustic transducers with respect to said plurality of known features for calibrating said plurality of acoustic transducers, said support frame and said plurality of acoustic transducers being moved with respect to said plurality of known features in at least one desired direction in each of said fewer than six scanning passes;
   recording position information for said support frame;
   recording respective outputs of said plurality of acoustic transducers in response to said plurality of known features; and
   comparing said outputs to expected outputs in response to said known features.

2. The method of claim 1, further comprising making only one scanning pass of said plurality of acoustic transducers with respect to said plurality of known features prior to or after said scanning of said material to be investigated.

3. The method of claim 1, wherein said plurality of acoustic transducers comprise a plurality of phased array acoustic transducers and further comprising:
- verifying that said position information is measured within a desired tolerance, and
- verifying that respective outputs of said plurality of phased acoustic transducers are all within a desired tolerance with respect to a respective wedge delay, a signal velocity, and a signal amplitude.

4. The method of claim 3, wherein said method comprises utilizing said position information to merge said respective outputs of said plurality of phased array acoustic transducers to verify that said plurality of phased array acoustic transducers are cooperating with each other within a desired tolerance.

5. The method of claim 1, comprising providing at least one guide member for said calibration block, and engaging said support frame with said at least one guide member for said scanning passes.

6. A method for calibrating a plurality of acoustic transducers, comprising:
- mounting said plurality of acoustic transducers to a support frame for simultaneous movement therewith;
- defining a plurality of known features within a calibration block;
- positioning said support frame and said plurality of acoustic transducers against said calibration block; and
- moving said support frame and said plurality of acoustic transducers with respect to said calibration block to produce calibration signals from said plurality of acoustic transducers, and, defining a recess within said calibration block, and wherein said step of moving comprises moving said support frame with said plurality of acoustic transducers within said recess.

7. The method of claim 6, further comprising providing respective engagement surfaces on said calibration block and said support frame, and moving said support frame relative to said calibration block while said respective engagement surfaces are engaged to thereby move said support frame along a predetermined path relative to said plurality of known features.

8. A system for calibrating a plurality of acoustic transducers, said plurality of acoustic transducers comprising at least one surface conforming member to engage a surface of a material to be acoustically scanned, said system comprising:
- a support frame for mounting said plurality of acoustic transducers such that said plurality of acoustic transducers are movable simultaneously with respect to said surface of material to be scanned;
- a calibration block defining a plurality of known features; and
- mating surfaces on said support frame and said calibration block which when engaged act to position said support frame and said plurality of acoustic transducers in a known orientation with respect to said known features, and further comprising a position sensor secured to said support frame, and a path defined by said calibration block for said position sensor to track a position of said plurality of acoustic transducers.

9. The system of claim 8, wherein said known orientation comprises an orientation of at least one rotational axis of said plurality of acoustic transducers.

10. The system of claim 8, wherein said mating surfaces further comprise at least one guide wall on said calibration block.

11. The system of claim 10, wherein said at least one guide wall is elongate whereby said support frame is moveable along a predetermined path on said calibration block while said plurality of acoustic transducers are constrained to remain in said known orientation with respect to said plurality of known features.

* * * * *